US012419749B2

(12) United States Patent
Aviv et al.

(10) Patent No.: US 12,419,749 B2
(45) Date of Patent: Sep. 23, 2025

(54) ANCHOR CHANNEL TIP

(71) Applicant: Edwards Lifesciences Innovation (Israel) LTD., Caesarea (IL)

(72) Inventors: Ehud Aviv, Costa Mesa, CA (US); Tal Sheps, Givat Shmuel (IL); Haim Brauon, Beit Dagan (IL); Amit Peer, Rehovot (IL)

(73) Assignee: Edwards Lifesciences Innovation (Israel) Ltd., Caesarea (IL)

( * ) Notice: Subject to any disclaimer, the term of this patent is extended or adjusted under 35 U.S.C. 154(b) by 883 days.

(21) Appl. No.: 17/681,131

(22) Filed: Feb. 25, 2022

(65) Prior Publication Data

US 2022/0273436 A1 Sep. 1, 2022

Related U.S. Application Data

(63) Continuation of application No. PCT/IL2020/050925, filed on Aug. 25, 2020.
(Continued)

(51) Int. Cl.
*A61F 2/24* (2006.01)
*A61B 17/04* (2006.01)
(Continued)

(52) U.S. Cl.
CPC .......... *A61F 2/2466* (2013.01); *A61B 17/064* (2013.01); *A61B 17/068* (2013.01);
(Continued)

(58) Field of Classification Search
CPC ................ A61F 2/2466; A61F 2/2445; A61B 2017/0409; A61B 2017/0649; A61B 17/068; A61M 25/0082
See application file for complete search history.

(56) References Cited

U.S. PATENT DOCUMENTS

| 3,604,488 A | 9/1971 | Wishart et al. |
| 3,656,185 A | 4/1972 | Carpentier |

(Continued)

FOREIGN PATENT DOCUMENTS

| CN | 113331995 A | 9/2021 |
| EP | 0611561 A1 | 8/1994 |

(Continued)

OTHER PUBLICATIONS

Agarwal et al. Interventional Cardiology Perspective Functional Tricuspid Regurgitation, Circ Cardiovasc Interv 2009;2;2;565-573 (2009).

(Continued)

*Primary Examiner* — Sarah W Aleman
(74) *Attorney, Agent, or Firm* — Anya Adams

(57) ABSTRACT

An apparatus is provided, for use with a tissue anchor, the apparatus comprising an implant and an anchor-delivery tool. The implant is dimensioned to be advanced into a body of a subject. The tool comprises an anchor-delivery channel and an implant-gripping element. The anchor-delivery channel defines a lumen, and is dimensioned to be moveable within the implant. The implant-gripping element is disposed at a distal end portion of the anchor-delivery channel, and comprises multiple teeth configured to reversibly grip an inner wall of the implant during implantation of the tissue anchor via the anchor-delivery channel. Other embodiments are also described.

30 Claims, 7 Drawing Sheets

Related U.S. Application Data

(60) Provisional application No. 62/894,517, filed on Aug. 30, 2019.

(51) Int. Cl.
*A61B 17/064* (2006.01)
*A61B 17/068* (2006.01)

(52) U.S. Cl.
CPC .... *A61F 2/2445* (2013.01); *A61B 2017/0409* (2013.01); *A61B 2017/0649* (2013.01); *A61F 2220/0016* (2013.01); *A61F 2250/0098* (2013.01)

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup |
| 5,716,370 A | 2/1998 | Williamson et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,752,963 A | 5/1998 | Allard et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich et al. |
| 5,961,539 A | 10/1999 | Northrup et al. |
| 5,984,959 A | 11/1999 | Robertson et al. |
| 5,993,459 A | 11/1999 | Larsen et al. |
| 6,042,554 A | 3/2000 | Rosenman et al. |
| 6,045,497 A | 4/2000 | Schweich et al. |
| 6,050,936 A | 4/2000 | Schweich et al. |
| 6,059,715 A | 5/2000 | Schweich et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larré |
| 6,461,366 B1 | 10/2002 | Seguin |
| 6,470,892 B1 | 10/2002 | Forsell |
| 6,503,274 B1 | 1/2003 | Howanec et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |

(56) References Cited

U.S. PATENT DOCUMENTS

| | | | |
|---|---|---|---|
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Séguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Séguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,152 B1 | 7/2011 | Webler et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |

(56) References Cited

U.S. PATENT DOCUMENTS

| | | |
|---|---|---|
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0083538 A1 | 5/2003 | Adams et al. |
| 2003/0093148 A1 | 5/2003 | Bolling et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0167062 A1 | 9/2003 | Gambale et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0229350 A1 | 12/2003 | Kay |
| 2003/0229395 A1 | 12/2003 | Cox |
| 2004/0002735 A1 | 1/2004 | Lizardi et al. |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0049211 A1 | 3/2004 | Tremulis et al. |
| 2004/0059413 A1 | 3/2004 | Argento |
| 2004/0068273 A1 | 4/2004 | Fariss et al. |
| 2004/0106950 A1 | 6/2004 | Grafton et al. |

(56) References Cited

U.S. PATENT DOCUMENTS

| | | |
|---|---|---|
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075654 A1 | 4/2005 | Kelleher |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0234481 A1 | 10/2005 | Waller |
| 2005/0240199 A1 | 10/2005 | Martinek et al. |
| 2005/0251177 A1 | 11/2005 | Saadat et al. |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0173251 A1 | 8/2006 | Govari et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0212048 A1 | 9/2006 | Crainich |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0060922 A1 | 3/2007 | Dreyfuss |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0173931 A1 | 7/2007 | Tremulis et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0244554 A1 | 10/2007 | Rafiee et al. |
| 2007/0244556 A1 | 10/2007 | Rafiee et al. |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0033460 A1 | 2/2008 | Ziniti et al. |
| 2008/0035160 A1 | 2/2008 | Woodson et al. |
| 2008/0039935 A1 | 2/2008 | Buch et al. |

(56) References Cited

U.S. PATENT DOCUMENTS

| | | |
|---|---|---|
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228030 A1 | 9/2008 | Godin |
| 2008/0228223 A1 | 9/2008 | Alkhatib |
| 2008/0234729 A1 | 9/2008 | Page et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0277445 A1 | 11/2008 | Zergiebel et al. |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0294251 A1 | 11/2008 | Annest et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082797 A1 | 3/2009 | Fung et al. |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0094314 A1 | 4/2010 | Hernlund et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0280604 A1 | 11/2010 | Zipory et al. |
| 2010/0286628 A1 | 11/2010 | Gross |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144576 A1 | 6/2011 | Rothe et al. |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0053628 A1 | 3/2012 | Sojka et al. |
| 2012/0053642 A1 | 3/2012 | Lozier et al. |
| 2012/0065464 A1 | 3/2012 | Ellis et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0109155 A1 | 5/2012 | Robinson et al. |
| 2012/0143226 A1 | 6/2012 | Belson et al. |
| 2012/0143323 A1 | 6/2012 | Hasenkam et al. |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |

(56) References Cited

U.S. PATENT DOCUMENTS

| | | |
|---|---|---|
| 2013/0046373 A1 | 2/2013 | Cartledge et al. |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0218206 A1 | 8/2013 | Gadlage |
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keränen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163615 A1 | 6/2014 | Gadlage et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243855 A1 | 8/2014 | Sholev et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1* | 10/2015 | Sheps .................... A61B 34/20 623/2.11 |
| 2015/0282931 A1 | 10/2015 | Brunnett et al. |
| 2015/0351910 A1 | 12/2015 | Gilmore et al. |
| 2016/0008132 A1 | 1/2016 | Cabiri et al. |
| 2016/0029920 A1 | 2/2016 | Kronström et al. |
| 2016/0030034 A1 | 2/2016 | Graul et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0256149 A1 | 9/2016 | Sampson et al. |
| 2016/0256274 A1 | 9/2016 | Hayoz |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0346084 A1 | 12/2016 | Taylor et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0100119 A1 | 4/2017 | Baird et al. |
| 2017/0224489 A1 | 8/2017 | Starksen et al. |
| 2017/0245993 A1 | 8/2017 | Gross et al. |
| 2017/0296340 A1* | 10/2017 | Gross .................... A61F 2/2445 |
| 2018/0008409 A1 | 1/2018 | Kutzik et al. |
| 2018/0049875 A1* | 2/2018 | Iflah .................... A61F 2/2412 |
| 2018/0078354 A1 | 3/2018 | Cardinale et al. |
| 2018/0140420 A1 | 5/2018 | Hayoz et al. |
| 2018/0168803 A1 | 6/2018 | Pesce et al. |
| 2018/0228608 A1 | 8/2018 | Sheps et al. |
| 2018/0256334 A1 | 9/2018 | Sheps et al. |
| 2018/0280019 A1 | 10/2018 | Azar et al. |
| 2018/0289480 A1 | 10/2018 | D'ambra et al. |
| 2018/0296331 A1 | 10/2018 | Dixon et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0059876 A1 | 2/2019 | Decker et al. |
| 2019/0070004 A1 | 3/2019 | Iflah et al. |
| 2019/0091445 A1 | 3/2019 | House |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0159898 A1 | 5/2019 | Kutzik et al. |
| 2019/0175344 A1 | 6/2019 | Khairkhahan |
| 2019/0175345 A1 | 6/2019 | Schaffner et al. |
| 2019/0175346 A1 | 6/2019 | Schaffner et al. |
| 2019/0183648 A1 | 6/2019 | Trapp et al. |
| 2019/0240023 A1 | 8/2019 | Spence et al. |
| 2019/0290260 A1 | 9/2019 | Caffes et al. |
| 2019/0290431 A1 | 9/2019 | Genovese et al. |
| 2019/0321049 A1 | 10/2019 | Herman et al. |
| 2019/0343633 A1 | 11/2019 | Garvin et al. |
| 2020/0015810 A1 | 1/2020 | Piccirillo |
| 2020/0015971 A1* | 1/2020 | Brauon .................... A61F 2/2445 |
| 2020/0178956 A1 | 6/2020 | Mitelberg et al. |
| 2020/0289267 A1 | 9/2020 | Peleg et al. |
| 2020/0337840 A1 | 10/2020 | Reich |
| 2020/0390551 A1 | 12/2020 | McCarthy |
| 2021/0015475 A1 | 1/2021 | Lau |
| 2021/0052387 A1 | 2/2021 | Greenan et al. |
| 2021/0059820 A1 | 3/2021 | Clark et al. |
| 2021/0085461 A1 | 3/2021 | Neumark et al. |
| 2021/0093453 A1 | 4/2021 | Peleg et al. |
| 2021/0145584 A1 | 5/2021 | Kasher et al. |
| 2022/0071620 A1 | 3/2022 | Brauon et al. |
| 2022/0096232 A1 | 3/2022 | Skaro et al. |
| 2022/0110656 A1 | 4/2022 | Azar et al. |
| 2022/0142779 A1 | 5/2022 | Sharon |
| 2022/0176076 A1 | 6/2022 | Keidar |
| 2022/0233316 A1 | 7/2022 | Sheps et al. |
| 2022/0273436 A1 | 9/2022 | Aviv et al. |
| 2022/0313438 A1 | 10/2022 | Chappel-Ram |
| 2022/0323221 A1 | 10/2022 | Sharon et al. |
| 2023/0016867 A1 | 1/2023 | Tennenbaum |
| 2023/0218291 A1 | 7/2023 | Zarbatany et al. |
| 2023/0320856 A1 | 10/2023 | Zarbatany et al. |

(56) References Cited

U.S. PATENT DOCUMENTS

| | | |
|---|---|---|
| 2024/0008985 A1 | 1/2024 | Yuan et al. |
| 2024/0099736 A1 | 3/2024 | Elsheikh et al. |

FOREIGN PATENT DOCUMENTS

| | | |
|---|---|---|
| EP | 0614342 A1 | 9/1994 |
| EP | 1034753 A1 | 9/2000 |
| EP | 3531975 A1 | 9/2019 |
| JP | 2008272488 A | 11/2008 |
| JP | 2013509974 A | 3/2013 |
| JP | 2013517109 A | 5/2013 |
| JP | 2013517830 A | 5/2013 |
| JP | 2016511062 A | 4/2016 |
| JP | 2019517289 A | 6/2019 |
| WO | 9205093 A1 | 4/1992 |
| WO | 1992005093 A1 | 4/1992 |
| WO | 1993010714 A1 | 6/1993 |
| WO | 1996039963 A1 | 12/1996 |
| WO | 1996040344 A1 | 12/1996 |
| WO | 1997001369 A1 | 1/1997 |
| WO | 9846149 A1 | 10/1998 |
| WO | 1998046149 A1 | 10/1998 |
| WO | 1999033414 A1 | 7/1999 |
| WO | 1999063907 A1 | 12/1999 |
| WO | 1999063910 A1 | 12/1999 |
| WO | 2000009048 A1 | 2/2000 |
| WO | 2001056457 A1 | 8/2001 |
| WO | 2002085250 A2 | 10/2002 |
| WO | 02085250 A3 | 2/2003 |
| WO | 03047467 A1 | 6/2003 |
| WO | 2003047467 A1 | 6/2003 |
| WO | 2004012583 A2 | 2/2004 |
| WO | 2005021063 A2 | 3/2005 |
| WO | 2006116558 A2 | 11/2006 |
| WO | 2007080595 A2 | 7/2007 |
| WO | 2007098512 A1 | 9/2007 |
| WO | 2007136981 A2 | 11/2007 |
| WO | 2008014144 A2 | 1/2008 |
| WO | 2009160631 | 10/2009 |
| WO | 2010000454 A1 | 1/2010 |
| WO | 2010006905 A1 | 1/2010 |
| WO | 2010065274 A1 | 6/2010 |
| WO | 2010128502 A1 | 11/2010 |
| WO | 2011051942 A1 | 5/2011 |
| WO | WO-2011057282 A2 | 5/2011 |
| WO | 2011089401 A1 | 7/2011 |
| WO | 2011089601 A1 | 7/2011 |
| WO | 2011111047 A2 | 9/2011 |
| WO | 2011154942 A2 | 12/2011 |
| WO | 2012011108 A2 | 1/2012 |
| WO | 2012068541 A2 | 5/2012 |
| WO | 2012106346 A1 | 8/2012 |
| WO | 2012176195 A2 | 12/2012 |
| WO | 2013021375 A2 | 2/2013 |
| WO | 2012176195 A3 | 3/2013 |
| WO | 2013078497 A1 | 6/2013 |
| WO | 2014064694 A2 | 5/2014 |
| WO | 2014064964 A1 | 5/2014 |
| WO | 2014087402 A1 | 6/2014 |
| WO | 2014108903 A1 | 7/2014 |
| WO | 2014195786 A2 | 12/2014 |
| WO | 2015059699 A2 | 4/2015 |
| WO | 2015193728 A2 | 12/2015 |
| WO | 2016059639 A1 | 4/2016 |
| WO | 2016087934 A1 | 6/2016 |
| WO | 2016174669 A1 | 11/2016 |
| WO | 2019145941 A1 | 8/2019 |
| WO | 2019145947 A1 | 8/2019 |
| WO | 2019182645 A1 | 9/2019 |
| WO | 2019224814 A1 | 11/2019 |
| WO | 2020240282 A2 | 12/2020 |
| WO | 2021014440 A2 | 1/2021 |
| WO | 2021038559 A1 | 3/2021 |
| WO | 2021038560 A1 | 3/2021 |
| WO | 2022064401 A2 | 3/2022 |
| WO | 2022090907 A1 | 5/2022 |
| WO | 2022101817 A2 | 5/2022 |
| WO | 2022153131 A1 | 7/2022 |
| WO | 2022157592 A1 | 7/2022 |
| WO | 2022172108 A1 | 8/2022 |
| WO | 2022172149 A1 | 8/2022 |
| WO | 2022200972 A1 | 9/2022 |
| WO | 2022224071 A1 | 10/2022 |
| WO | 2022229815 A1 | 11/2022 |
| WO | 2022250983 A1 | 12/2022 |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.
Ahmadi, Ali et al. "Percutaneously adjustable pulmonary artery band." The Annals of thoracic surgery 60 (1995): S520-S522.
Alfieri et al., "An effective technique to correct anterior mitral leaflet prolapse," J Card 14(6):468-470 (1999).
Alfieri et al., "The double orifice technique in mitral valve repair: a simple solution for complex problems," Journal of Thoracic Cardiovascular Surgery 122:674-681 (2001).
Alfieri et al."Novel Suture Device for Beating-Heart Mitral Leaflet Approximation", Ann Thorac Surg. 2002, 74:1488-1493.
Alfieri, "The edge-to-edge repair of the mitral valve," [Abstract] 6th Annual NewEra Cardiac Care: Innovation&Technology, Heart Surgery Forum pp. 103. (2000).
Amplatzer Cardiac Plug brochure (English pages), AGA Medical Corporation (Plymouth, MN) (copyright 2008-2010, downloaded Jan. 11, 2011).
AMPLATZER® Cribriform Occluder. A patient guide to Percutaneous, Transcatheter, Atrial Septal Defect Closuer, AGA Medical Corporation, Apr. 2008.
AMPLATZER® Septal Occluder. A patient guide to the Non-Surgical Closuer of the Atrial Septal Defect Using the AMPLATZER Septal Occluder System, AGA Medical Corporation, Apr. 2008.
Assad, Renato S. "Adjustable Pulmonary Artery Banding." (2014).
Brennan, Jennifer, 510(k) Summary of safety and effectiveness, Jan. 2008.
Daebritz, S. et al. "Experience with an adjustable pulmonary artery banding device in two cases: initial success-midterm failure." The Thoracic and cardiovascular surgeon 47.01 (1999): 51-52.
Dang NC et al. "Simplified Placement of Multiple Artificial Mitral Valve Chords," The Heart Surgery Forum #2005-1005, 8 (3) (2005).
Dictionary.com definition of "lock", Jul. 29, 2013.
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
Elliott, Daniel S., Gerald W. Timm, and David M. Barrett. "An implantable mechanical urinary sphincter: a new nonhydraulic design concept." Urology52.6 (1998): 1151-1154.
Langer et al. Ring plus String: Papillary muscle repositioning as an adjunctive repair technique for ischemic mitral regurgitation, The Journal of Thoracic Cardiovascular surgery vol. 133 No. 1, Jan. 2007.
Langer et al. RING+STRING, Successful Repair technique for ischemic mitral regurgitation with severe leaflet Tethering, The Department of Thoracic Cardiovascular surgery, Hamburg, Germany, Nov. 2008.
Maisano, The double-orifice technique as a standardized approach to treat mitral . . ., European Journal of Cardio-thoracic Surgery 17 (2000) 201-205.
Odell JA et al., "Early Results o4yf a Simplified Method of Mitral Valve Annuloplasty," Circulation 92:150-154 (1995).
O'Reilly S et al., "Heart valve surgery pushes the envelope," Medtech Insight 8(3): 73, 99-108 (2006).
Park, Sang C. et al. "A percutaneously adjustable device for banding of the pulmonary trunk." International journal of cardiology 9.4 (1985): 477-484.

(56) References Cited

OTHER PUBLICATIONS

Swain CP et al., "An endoscopically deliverable tissue-transfixing device for securing biosensors in the gastrointestinal tract," Gastrointestinal Endoscopy 40(6): 730-734 (1994).
Swenson, O. An experimental implantable urinary sphincter. Invest Urol. Sep. 1976;14(2):100-3.
Swenson, O. and Malinin, T.I., 1978. An improved mechanical device for control of urinary incontinence. Investigative urology, 15(5), pp. 389-391.
Swenson, Orvar. "Internal device for control of urinary incontinence." Journal of pediatric surgery 7.5 (1972): 542-545.
Tajik, Abdul, "Two dimensional real-time ultrasonic imaging of the heart and great vessels", Mayo Clin Proc. vol. 53:271-303, 1978.
Alfieri et al., "The edge to edge technique," The European Association for Cardio-Thoracic Surgery 14th Annual Meeting October 7-11, Book of Procees. (2000).
Sutton E.E. et al., "Biologically Inspired Catheter for Endovascular Sensing and Navigation", Scientific Reports Journal, vol. 10, 5643, Mar. 27, 2020, DOI https://doi.org/10.1038/s41598-020-62360-w.
Agarwal et al. International Cardiology Perspective Functional Tricuspid Regurgitation, Circ Cardiovasc Interv 2009;2;2;565-573 (2009).
Odell JA et al., "Early Results 04yf a Simplified Method of Mitral Valve Annuloplasty," Circulation 92:150-154 (1995).

\* cited by examiner

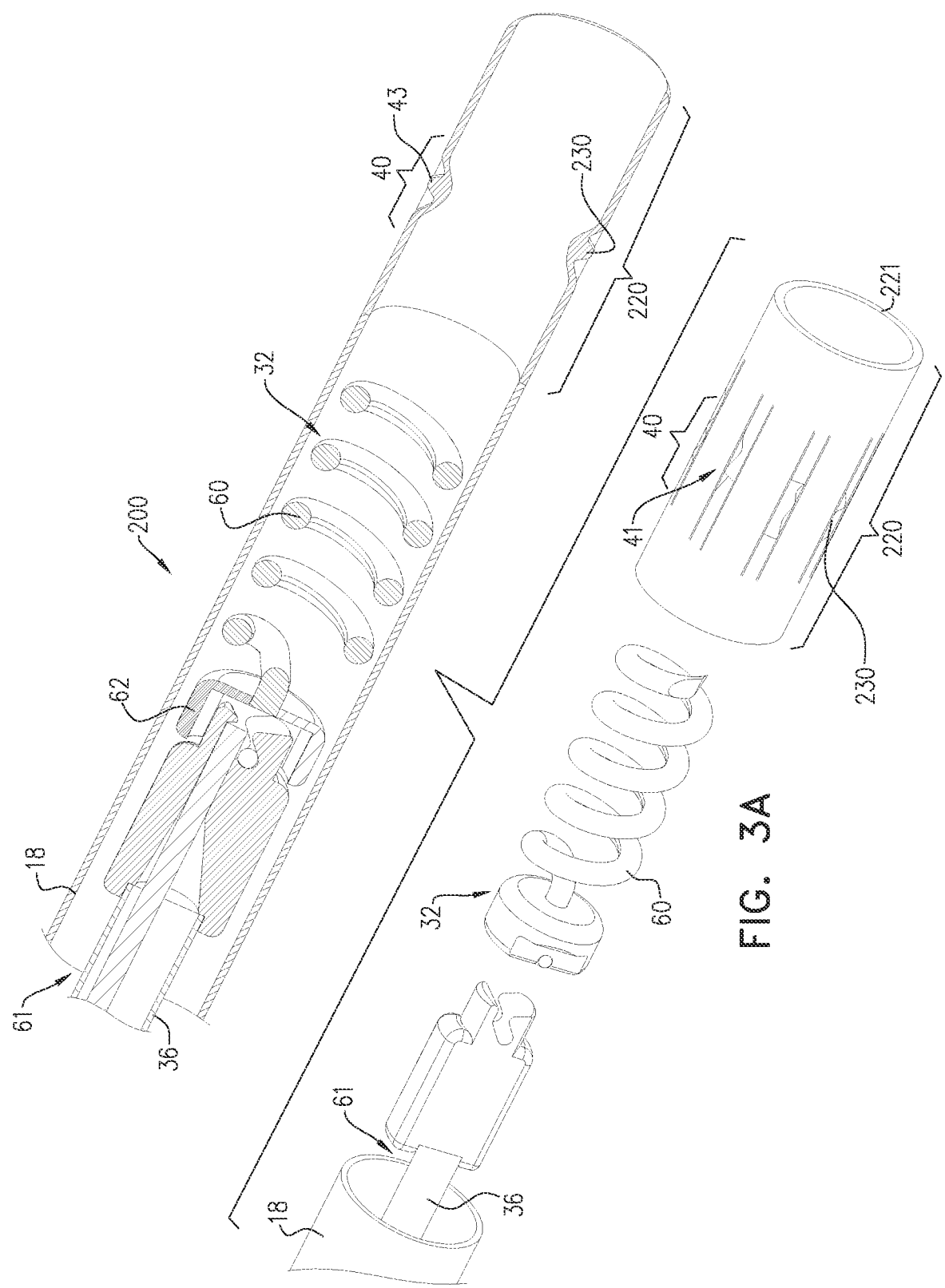

ANCHOR CHANNEL TIP

CROSS-REFERENCE TO RELATED APPLICATIONS

This application is a Continuation of International Patent Application PCT/IL2020/050925 to Iflah et al., filed Aug. 25, 2020, which published as WO 2021/038559, and which claims the benefit of U.S. Provisional Patent Application 62/894,517, filed Aug. 30, 2019, each of which is incorporated by reference herein for all purposes.

BACKGROUND

Annuloplasty structures comprising a flexible material through which anchors are delivered tend to twist and warp as a result of passage of the anchor through the material of the annuloplasty structure. It is therefore often advantageous to provide devices and techniques to facilitate deployment of the tissue anchor through the flexible material of the annuloplasty structure while minimizing or eliminating twisting or warping of the flexible material during deployment of the anchor.

SUMMARY OF THE INVENTION

This summary is meant to provide some examples and is not intended to be limiting of the scope of the invention in any way. For example, any feature included in an example of this summary is not required by the claims, unless the claims explicitly recite the features. Also, the features described can be combined in a variety of ways. Various features and steps as described elsewhere in this disclosure can be included in the examples summarized here.

A tubular structure is used to advance toward a tissue site of a subject an anchor driver used to drive a tissue anchor into tissue of a subject. The tubular structure has a distal end portion comprising an implant-gripping element that is configured to temporarily grip material (e.g., flexible material) of an annuloplasty structure, in accordance with some applications of the present invention.

For some applications of the present invention, the implant-gripping element comprises a plurality of teeth which reversibly grip the material of the annuloplasty structure during deploying, or driving, a tissue anchor through material of the annuloplasty structure so as to anchor the annuloplasty structure to tissue of the subject.

For some applications of the present invention, the implant-gripping element comprises a deformable element which changes its structural configuration as a tissue anchor is passed with respect to and engages the deformable element. This is advantageous because the tubular structure is able to move freely within a lumen of the annuloplasty structure and only engage and grip the annuloplasty structure once the desired location of tissue has been reached and it has been determined that in this location, a tissue anchor be driven into tissue.

There is therefore provided, in accordance with an application of the present invention, a system and/or apparatus, for use with a tissue anchor, the system/apparatus including an implant, dimensioned to be advanced into a body of a subject and an anchor-delivery tool. The anchor delivery tool can include an anchor-delivery channel, shaped to define a lumen therethrough, the lumen having a diameter, and the channel being dimensioned to be moveable within a lumen of the implant. The anchor-delivery tool can also include an implant-gripping element disposed at a distal end portion of the anchor-delivery channel. The implant-gripping element can be configured to reversibly grip an inner wall of the implant during implantation of the tissue anchor via the anchor-delivery channel.

In an application, the implant-gripping element includes a radiopaque material.

In an application, the implant includes a flexible material, and the flexible material of the implant encases a distal portion of the channel.

In an application, the implant-gripping element includes a plurality of teeth which increase friction between the implant and the anchor-delivery channel.

In an application, the plurality of teeth are cut from a distal portion of a cylinder coupled to the distal end portion of the anchor-delivery channel.

In an application:
  each one of the plurality of teeth includes a respective elongate element that is aligned with a longitudinal axis of the distal end portion of the anchor-delivery channel,
  a portion of the implant surrounds the plurality of elongate elements, and
  the elongate elements are spaced apart from one another such that the plurality of elongate elements are configured to grip the portion of the implant.

In an application, a respective distal portion of each of the plurality of teeth are configured to grip the implant.

In an application, the implant includes a braided fabric, and the distal portions of the plurality of teeth are configured to reversibly ensnare the braided fabric.

In an application, the system/apparatus further includes the tissue anchor, and the tissue anchor includes:
  an anchor head; and
  a tissue-engaging member, coupled to the anchor head, extending distally away from the anchor head until a distal tip of the tissue-engaging member, and configured to anchor the anchor to the tissue.

In an application, the tissue-engaging member includes a helical tissue-engaging member, and the implant-gripping element is configured to reversibly grip the implant and prevent twisting of the implant during corkscrewing of the helical tissue-engaging member with respect to the implant.

In an application, the system/apparatus further includes an anchor driver slidable through the lumen of the anchor-delivery channel, the anchor driver including:
  a longitudinal shaft, having a flexible distal portion and a distal end; and
  a deployment element coupled to the distal end of the shaft, and reversibly couplable to the anchor head.

In an application, the implant-gripping element includes at least one deformable element configured to change shape from a resting state to a gripping state in response to passage of the tissue anchor alongside the deformable element.

In an application, the implant-gripping element includes a plurality of deformable elements disposed circumferentially with respect to the distal end portion of the anchor-delivery channel.

In an application, the deformable element is shaped so as to define an elongate tine having a straight portion and a curved portion in the resting state of the deformable element, and in the gripping state of the deformable element, the anchor is configured to radially push against the curved portion so as to straighten the curved portion and responsively, longitudinally lengthen the deformable element.

In an application, in the gripping state, a distal end of the deformable element extends beyond a distal end of the anchor-delivery channel.

In an application, the at least one deformable element includes a plurality of elongate tines, and the anchor is configured to radially push against the respective curved portions of the plurality of elongate tines.

In an application, the distal ends of the plurality of elongate tines are configured to increase surface area contact with the inner wall of the implant in the gripping state of the deformable element.

In an application:
the deformable element is shaped so as to define a laterally-moveable lateral projection,
in the resting state of the deformable element, a lateral-most portion of the projection is aligned with a lateral surface of the anchor-delivery channel, and
in the gripping state, the anchor is configured to radially push against the lateral projection so as to extend the lateral-most portion of the projection beyond the lateral surface of the anchor-delivery channel.

In an application, the at least one deformable element includes a plurality of lateral projections, and the anchor is configured to radially push against the plurality of lateral projections.

In an application, the plurality of lateral projections are configured to increase surface area contact with the inner wall of the implant in the gripping state of the deformable element.

There is further provided, in accordance with an application of the present invention, a method including positioning an implant along an annulus of a heart valve of a subject. The implant is optimally dimensioned to be advanced into a body of the subject. The method can further include advancing an anchor-delivery tool with respect to the implant.

In some applications, the anchor-delivering tool includes an anchor-delivery channel, shaped to define a lumen therethrough, the lumen having a diameter. The channel can be dimensioned to be moveable within a lumen of the implant.

In some applications, the anchor-delivering tool includes an implant-gripping element disposed at a distal end portion of the anchor-delivery channel, the implant-gripping element being configured to reversibly grip a portion or wall of the implant (e.g., an inner wall of the implant, etc.) during implantation of the tissue anchor via the anchor-delivery channel.

The method can further include gripping a first portion of the implant using the implant-gripping element, and during the gripping of the first portion, anchoring the first portion of the implant to the annulus using a tissue anchor deliverable through the anchor-delivery channel.

In an application, the method further includes:
decoupling the implant-gripping element from the first portion of the implant subsequently to the anchoring of the first portion of the implant to the annulus;
moving the anchor-delivery channel to a second portion of the implant;
gripping the second portion of the implant using the implant-gripping element; and
during the gripping of the second portion, anchoring the second portion of the implant to the annulus using a second tissue anchor deliverable through the anchor-delivery channel.

In an application, the implant-gripping element includes a radiopaque material.

In an application, the implant includes a flexible material, and the flexible material of the implant encases a distal portion of the channel.

In an application, the implant-gripping element includes a plurality of teeth, and gripping the first portion of the implant includes increasing friction between the first portion of the implant and the anchor-delivery channel.

In an application, the plurality of teeth are cut from a distal portion of a cylinder coupled to the distal end portion of the anchor-delivery channel, and gripping the first portion of the implant includes sandwiching the first portion of the implant between respective distal ends of the plurality of teeth and the annulus.

In an application:
each one of the plurality of teeth includes a respective elongate element that is aligned with a longitudinal axis of the distal end portion of the anchor-delivery channel,
a lateral portion of the implant surrounds the plurality of elongate elements,
the elongate elements are spaced apart from one another, and
gripping the first portion of the implant includes gripping the lateral portion of the implant by the elongate elements.

In an application, a respective distal portion of each of the plurality of teeth are configured to grip the implant, and gripping the first portion of the implant includes sandwiching the first portion of the implant between respective distal ends of the plurality of teeth and the annulus.

In an application, the implant includes a braided fabric, and gripping the first portion of the implant includes reversibly ensnaring the braided fabric by the plurality of teeth.

In an application:
the tissue anchor includes:
an anchor head; and
a tissue-engaging member, coupled to the anchor head, extending distally away from the anchor head until a distal tip of the tissue-engaging member, and configured to anchor the anchor to the tissue, and
anchoring the first portion of the implant to the annulus includes anchoring the first portion using the tissue anchor including the anchor head and the tissue-engaging member.

In an application:
the tissue-engaging member includes a helical tissue-engaging member,
anchoring the first portion of the implant includes corkscrewing the helical tissue-engaging member with respect to the first portion of the implant and into the annulus, and
gripping the first portion of the implant includes using the implant-gripping element to reversibly grip the first portion of the implant and prevent twisting of the implant during the corkscrewing of the helical tissue-engaging member with respect to the first portion of the implant.

In an application, the method further includes sliding through the lumen of the anchor-delivery channel an anchor driver including:
a longitudinal shaft, having a flexible distal portion and a distal end; and
a deployment element coupled to the distal end of the shaft, and reversibly couplable to the anchor head.

In an application, the implant-gripping element includes at least one deformable element configured to change shape from a resting state to a gripping state in response to passage of the tissue anchor alongside the deformable element, and the method further includes changing the shape of the deformable element by passing the tissue anchor alongside the deformable element.

In an application, the implant-gripping element includes a plurality of deformable elements disposed circumferentially with respect to the distal end portion of the anchor-delivery channel.

In an application, the deformable element is shaped so as to define an elongate tine having a straight portion and a curved portion in the resting state of the deformable element, and passing the tissue anchor alongside the deformable element includes radially pushing the anchor against the curved portion, and by the pushing, straightening the curved portion and responsively, longitudinally lengthening the deformable element such that the deformable element assumes the gripping state.

In an application, in the gripping state, longitudinally lengthening the deformable element includes extending a distal end of the deformable element beyond a distal end of the anchor-delivery channel.

In an application, the at least one deformable element includes a plurality of elongate tines, and radially pushing the anchor includes radially pushing the anchor against the respective curved portions of the plurality of elongate tines.

In an application, gripping the first portion of the implant includes increasing surface area contact with the inner wall of the implant in the gripping state of the deformable element using the distal ends of the plurality of elongate tines.

In an application:
the deformable element is shaped so as to define a laterally-moveable lateral projection,
in the resting state of the deformable element, a lateral-most portion of the projection is aligned with a lateral surface of the anchor-delivery channel,
in the gripping state, the anchor is configured to radially push against the lateral projection so as to extend the lateral-most portion of the projection beyond the lateral surface of the anchor-delivery channel,
passing the tissue anchor alongside the deformable element includes radially pushing the anchor against the lateral projection, and by the pushing, extending the lateral-most portion of the projection beyond the lateral surface of the anchor-delivery channel.

In an application, the at least one deformable element includes a plurality of lateral projections, and pushing the anchor against the lateral projection includes radially pushing the anchor against the plurality of lateral projections.

In an application, radially pushing the anchor against the plurality of lateral projections includes increasing surface area contact with the inner wall of the implant in the gripping state of the deformable element.

The foregoing method(s) and other methods herein can be performed on a living animal or on a simulation, such as on a cadaver, cadaver heart, simulator (e.g. with the body parts, tissue, etc. being simulated), etc.

The present invention will be more fully understood from the following detailed description of applications thereof, taken together with the drawings, in which:

BRIEF DESCRIPTION OF THE DRAWINGS

FIGS. 3A-C are schematic illustrations of an example of an implant-gripping element comprising another deformable element.

DETAILED DESCRIPTION OF EMBODIMENTS

Figure 1:
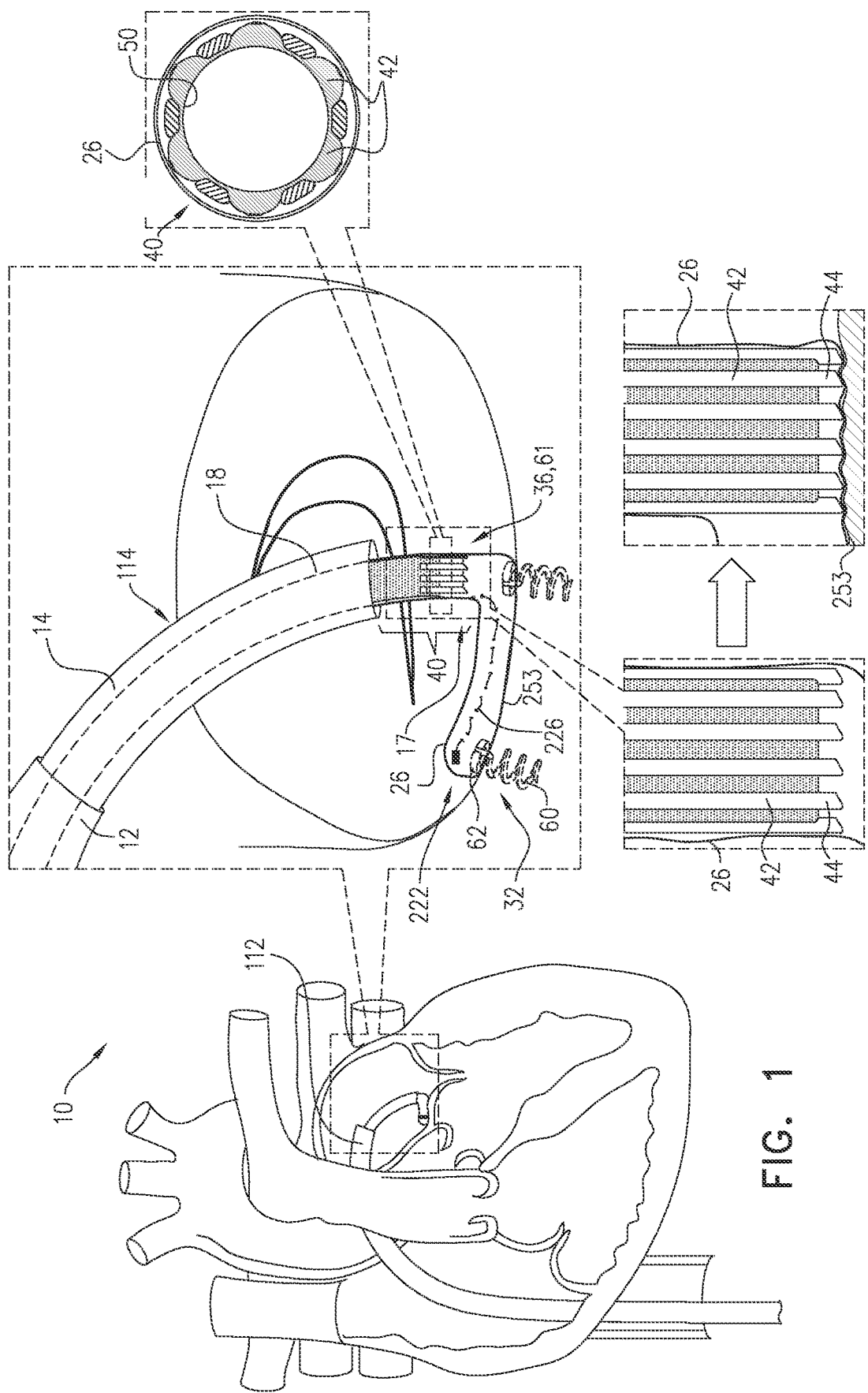
FIG. 1 is a schematic illustration of an example of an implant-gripping element comprising a plurality of teeth.

Reference is now made to FIG. 1, which is a schematic illustration of a system 10 providing one or more rotationally-controlled steering catheters configured for delivering an implant to a heart of a subject, in accordance with some applications of the present invention. FIG. 1 shows a distal portion of an implant that comprises an annuloplasty ring structure 222 (i.e., an implant, e.g., an annuloplasty band) comprising a flexible sleeve 26. The implant is dimensioned to be advanced into a body of a subject. System 10 comprises an anchor-delivery tool comprising an implant-decoupling channel 18. As described hereinbelow, channel 18 is used to facilitate delivery of tissue anchors through channel 18 and into a lumen of sleeve 26. Thus, channel 18 functions as an anchor-delivery channel. Channel 18 is shaped so as to define a lumen having a diameter. Sleeve 26 comprises a flexible material which encases a distal portion of channel 18. Channel 18 is dimensioned to be moveable within a lumen of the implant. An implant-gripping element 40 is disposed at a distal end portion of channel 18. Implant-gripping element 40 is configured to reversibly grip an inner wall 50 of the implant during implantation of tissue anchor 32 via channel 18.

Sleeve 26 typically comprises a braided fabric mesh, e.g., comprising polyethylene terephthalate (such as Dacron™). Sleeve 26 can be configured to be placed only partially around a cardiac valve annulus (i.e., to assume a C-shape), and, once anchored in place, to be contracted so as to circumferentially tighten the valve annulus. Though optionally, the ring structure can also be configured to be placed entirely around the valve annulus.

Sleeve 26 has a tubular lateral wall 253 that (i) circumscribes a central longitudinal axis of the sleeve, and (ii) defines the lumen of the sleeve.

In order to tighten the annulus, annuloplasty ring structure 222 comprises a flexible elongated contraction member 226 that extends along sleeve 26. Elongated contraction member 226 comprises a wire, a ribbon, a rope, or a band, which typically comprises a flexible and/or superelastic material, e.g., nitinol, polyester, stainless steel, or cobalt chrome. For some applications, the wire comprises a radiopaque material. For some applications, contraction member 226 comprises a braided polyester suture (e.g., Ticron). For some applications, contraction member 226 is coated with polytetrafluoroethylene (PTFE). For some applications, contraction member 226 comprises a plurality of wires that are intertwined to form a rope structure.

For some applications, annuloplasty ring structure 222 comprises an adjustment mechanism as described with reference to PCT application PCT/IL2016/050433 to Iflah, et al., which published as WO 2016/174669, and which is incorporated herein by reference. The adjustment mechanism facilitates contracting and expanding of annuloplasty ring structure 222 so as to facilitate adjusting of a perimeter of the annulus and leaflets of the cardiac valve. The adjustment mechanism can comprise a rotatable structure (e.g., a spool).

System 10 can comprise a concentric arrangement of tubes defining an implant-delivery tool. System 10 can comprise a first, outer catheter 12 comprising a sheath configured for transluminal advancement through vasculature of a subject. For some applications of the present invention, outer catheter 12 comprises a sheath configured for advancement through a femoral artery toward an interatrial septum of a heart of a subject. A distal end portion 112 of outer catheter 12 is configured to pass through the transatrial septum of the subject, and to be oriented in a desired spatial orientation within the left atrium. System 10 comprises a second catheter, or guide catheter 14, comprising a distal end portion 114 that is configured to pass through catheter 12 (i.e., a primary lumen thereof), to become disposed outside of a distal end of the outer catheter, and to be oriented in a desired spatial orientation within the left atrium.

Distal end portion 112 of outer catheter 12 is steerable. That is, distal end portion 112 is deflectable with respect to an immediately more proximal portion of catheter 12 (e.g., by using extracorporeal elements of system 10). Distal end portion 114 of inner catheter 14 is steerable. That is, distal end portion 114 is deflectable with respect to an immediately more proximal portion of catheter 14 (e.g., by using extracorporeal elements of system 10).

Guide catheter 14 is steerable to a desired spatial orientation in order to facilitate advancing and implantation of an implant in a body cavity of the subject.

For applications in which system 10 is used to deliver an implant to the mitral valve of the subject, often, outer catheter 12 is configured for initial advancement through vasculature of the subject until a distal end of catheter 12 is positioned in the left atrium. The distal steerable end portion of catheter 12 is then steered such that distal end of catheter 12 is positioned in a desired spatial orientation within the left atrium. The steering procedure can be performed with the aid of imaging, such as fluoroscopy, transesophageal echo, and/or echocardiography. Following the steering of the distal end portion of catheter 12, guide catheter 14 (which houses annuloplasty ring structure 222) is advanced through catheter 12 in order to facilitate delivery and implantation of structure 222 along the annulus of the mitral valve. During the delivery, at least a portion of steerable distal end portion 114 is exposed from the distal end of catheter 12 and is thus free for steering toward the annulus of the mitral valve, as is described hereinbelow.

During delivery of sleeve 26 to the annulus of the cardiac valve, sleeve 26 is disposed within a lumen of catheter 14 and can be aligned longitudinally with a longitudinal axis of catheter 14.

In addition, in some applications, system 10 comprises a plurality of anchors 32, typically between about 5 and about 20 anchors, such as about 10 or about 16 anchors. Each anchor 32 comprises a tissue-coupling element 60 (e.g., a helical tissue-coupling element), and a tool-engaging head 62 (e.g., a non-helically-shaped portion), or an anchor head, fixed to one end of the tissue-coupling element. Each tissue-coupling element 60 defines a respective tissue-engaging member. Each anchor 32 is deliverable to the target tissue site by a deployment element of an anchor driver 36 of an anchor deployment manipulator 61. Driver 36 comprises (1) a longitudinal shaft having a flexible distal portion and a distal end, and (2) a deployment element coupled to the distal end of the shaft. The deployment element of driver 36 is reversibly couplable to tool-engaging head 62 of anchor 32. When sleeve 26 is disposed along the annulus of the cardiac valve, deployment manipulator 61 is configured to advance within a lumen of sleeve 26 and deploy each anchor 32 from within sleeve 26 through a wall of sleeve 26 and into cardiac tissue, thereby anchoring sleeve 26 around a portion of the valve annulus.

Typically, but not necessarily, anchors 32 comprise a biocompatible material such as stainless steel 316 LVM. For some applications, anchors 32 comprise nitinol. For some applications, anchors 32 are coated fully or partially with a non-conductive material.

Deployment manipulator 61 comprises anchor driver 36 and the deployment element. For some applications, deployment manipulator 61 comprises an implant-decoupling channel 18. As described hereinbelow, channel 18 is used to facilitate delivery of tissue anchors through channel 18 and into a lumen of sleeve 26. Thus, channel 18 functions as an anchor-delivery channel.

Sleeve 26 is disposed within a lumen of guide catheter 14. Implant-decoupling channel 18 is advanceable within a lumen of sleeve 26. A distal end 17 of implant-decoupling channel 18 is placeable in contact with an inner wall of sleeve 26, e.g., at a distal end thereof.

For some applications, channel 18 is steerable.

For some applications, manipulator 61 advances within channel 18. For some applications, system 10 comprises a plurality of anchor drivers of manipulator 61, each driver 36 being coupled to a respective anchor 32. Each driver 36 is advanced within channel 18 in order to advance and implant anchor 32 in tissue. Following implantation of anchor 32, anchor 32 is decoupled from driver 36, as described herein, and driver 36 is removed from within channel 18. A subsequent anchor 32 is then advanced within channel 18 while coupled to a driver 36 (e.g., a new driver).

As will be described hereinbelow, a first one of anchors 32 is configured to be deployed through an end wall, or an end, of sleeve 26 into cardiac tissue, when sleeve 26 is positioned along the annulus of the valve. Following the deployment of the first tissue anchor, a distal portion of sleeve 26 is slid distally off a portion of implant-decoupling channel 18. In order to decouple sleeve 26 distally from a portion of outer surface of channel 18, (1) a proximal force is applied to channel 18, while (2) a reference-force tube (disposed proximally to sleeve 26) is maintained in place in a manner in which a distal end of the reference-force tube provides a reference force to sleeve 26, thereby facilitating freeing of a successive portion of sleeve 26 from around channel 18. Channel 18 is then positioned at a successive location within the lumen of sleeve 26 while the reference-force tube and/or catheter 14 is steered toward a successive location along the annulus of the valve (as will be described hereinbelow). Consequently, the successive portion of sleeve 26 provides a free lumen for advancement of a successive anchor 32 and deployment of the anchor through the wall of the sleeve at the successive portion thereof. Such freeing of the successive portion of sleeve 26 creates a distance between successive anchors deployed from within the lumen of sleeve 26.

For some applications, sleeve 26 comprises a plurality of radiopaque markers, which are positioned along the sleeve at respective longitudinal sites. The markers can provide an indication in a radiographic image (such as a fluoroscopy image) of how much of the sleeve has been deployed at any given point during an implantation procedure, in order to enable setting a desired distance between anchors 32 along the sleeve. For some applications, the markers comprise a radiopaque ink, but other configurations are also possible.

As described hereinabove, implant-gripping element 40 is disposed at a distal end portion of channel 18. For some applications, as shown, element 40 comprises a plurality of teeth 44 which extend beyond the distal end portion of channel 18 and beyond a distal end of the lumen defined by channel 18. The plurality of teeth 44 are circumferentially disposed around a circumference of the distal end portion of channel 18. For some applications of the present invention, each one of teeth 44 is jagged. The plurality of teeth 44 are configured to increase friction between channel 18 and the implant. Collectively, the plurality of teeth 44 form a series of peaks and valleys which increase surface area contact between channel 18 and inner wall 50 of sleeve 26. For some applications of the present invention, teeth 44 are slanted. For some applications of the present invention, teeth 44 are rectangular. In either application, teeth 44 are configured to create increased surface area between the distal end of channel 18 and sleeve 26. Additionally, teeth 44 are configured to reversibly grip sleeve 26 by pressing against sleeve 26.

As shown, each one of teeth 44 is at a distal end of a respective elongate element 42 that is aligned with a longitudinal axis of the distal end portion of anchor-delivery channel 18. Elongate elements 42 are spaced apart from one another such that the plurality of elongate elements 42 are configured to grip the portion of the implant. Collectively, the plurality of elongate elements 42 form a series of peaks and valleys which increase surface area contact between channel 18 and inner wall 50 of sleeve 26. Elongate elements 42 increase surface area between the lateral surface of channel 18 and inner wall 50 of sleeve 26 while teeth 44 increase surface area between the distal opening of channel 18 and inner wall 50 of sleeve 26. For some applications of the present invention, a respective distal portion of each of the plurality of teeth 44 are configured to grip the implant. That is, the implant comprises a braided fabric, and the distal portions of the plurality of teeth 44 are configured to reversibly ensnare the braided fabric.

For some applications of the present invention, teeth 44 and/or elongate elements 42 comprise radiopaque material.

The portion of sleeve 26 reversibly engaged and gripped by teeth 44 is the portion of sleeve 26 that is sandwiched between the distal end channel 18 (i.e., the distal ends of teeth 44) and tissue. For some applications of the present invention, elongate elements 42 reversibly grip and engage lateral portions of sleeve 26 proximal to the portion of sleeve 26 that is sandwiched between the distal end channel 18 (i.e., the distal ends of teeth 44) and tissue. That is, elongate elements 42 are spaced apart from each other creating a series of peaks and valleys which increase surface area so as to increase friction between elongate elements 42 and sleeve 26.

For some applications of the present invention, the plurality of teeth 44 are cut from a distal portion of a cylinder coupled to the distal end portion of anchor-delivery channel 18. For some applications of the present invention, the plurality of teeth 44 are cut from a distal portion of anchor-delivery channel 18.

Prior to delivery of tissue anchor 32 into tissue of the subject, a portion of sleeve 26 is sandwiched between the distal end of channel 18 (i.e., the distal ends of teeth 44) and the tissue. This is because a distal end of channel 18 contacts inner wall 50 of sleeve 26. An anchor 32 is passed through a lumen of channel 18 and toward the target tissue site by a deployment element of anchor driver 36 of an anchor deployment manipulator 61. During the driving of the tissue anchor through material of sleeve 26 and subsequently into the target tissue, implant-gripping element 40 grips the material of sleeve 26 to prevent or minimize distortion, movement, deformation, twisting, torsion, bunching, and any other relative movement of sleeve 26 with respect to tissue. For applications in which tissue-coupling element 60 of anchor 32 comprises a helical tissue coupling-element, implant-gripping element 40 prevents or minimizes twisting or torsion of sleeve 26 during the driving of anchor 32 through the material of sleeve 26.

Once anchor 32 is delivered through sleeve 26, teeth 44 and elongate elements 42 are decoupled from sleeve 26 (and thereby the grip on sleeve 26 by gripping element 40 is removed), by simply applying a pulling force to channel 18. Since sleeve 26 is firmly anchored to tissue of the annulus by anchor 32, a slight upward pulling force to channel 18 overcomes the reversible grip teeth 44 and elongate elements 42 temporarily have on sleeve 26.

It is to be noted that the gripping and ungripping of gripping element 40 can occur repeatedly throughout the process of anchoring sleeve 26 to tissue of the annulus. For each anchor delivery, gripping element 40 grips sleeve 26 as each anchor 32 is deployed to anchor a given portion of the implant to the annulus, and once anchor 32 has been deployed, gripping element 40 is pulled proximally in order to reverse the gripping of sleeve 26 by gripping element 40. Channel 18 is then moved to a different portion of the implant, and the gripping of sleeve 26 by gripping element 40 occurs once more as another anchor is deployed to anchor the different portion of the implant to the annulus.

Figure 2A:
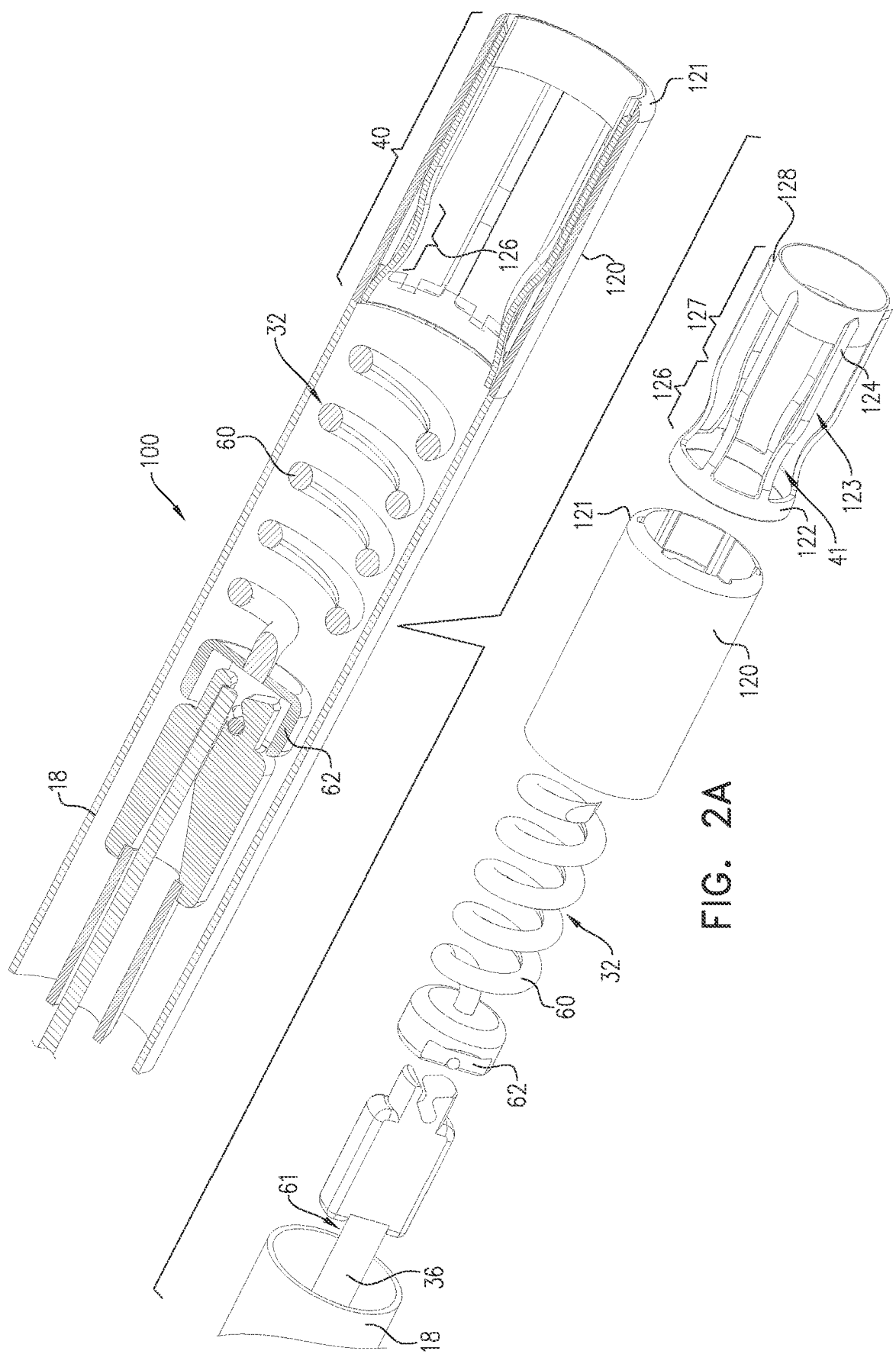
FIGS. 2A-C are schematic illustrations of an example of an implant-gripping element comprising a deformable element.
Figure 2B:
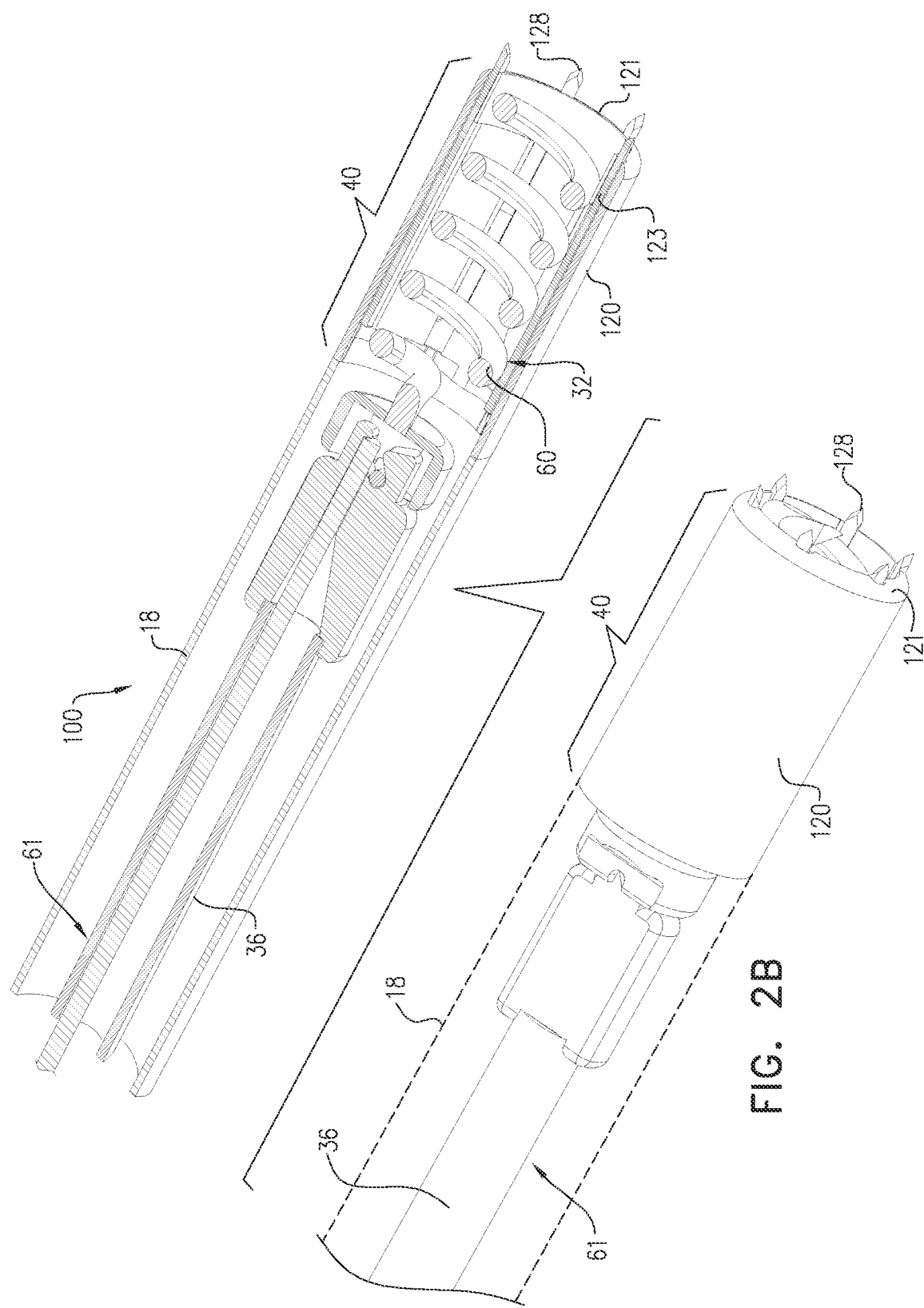
Figure 2C:
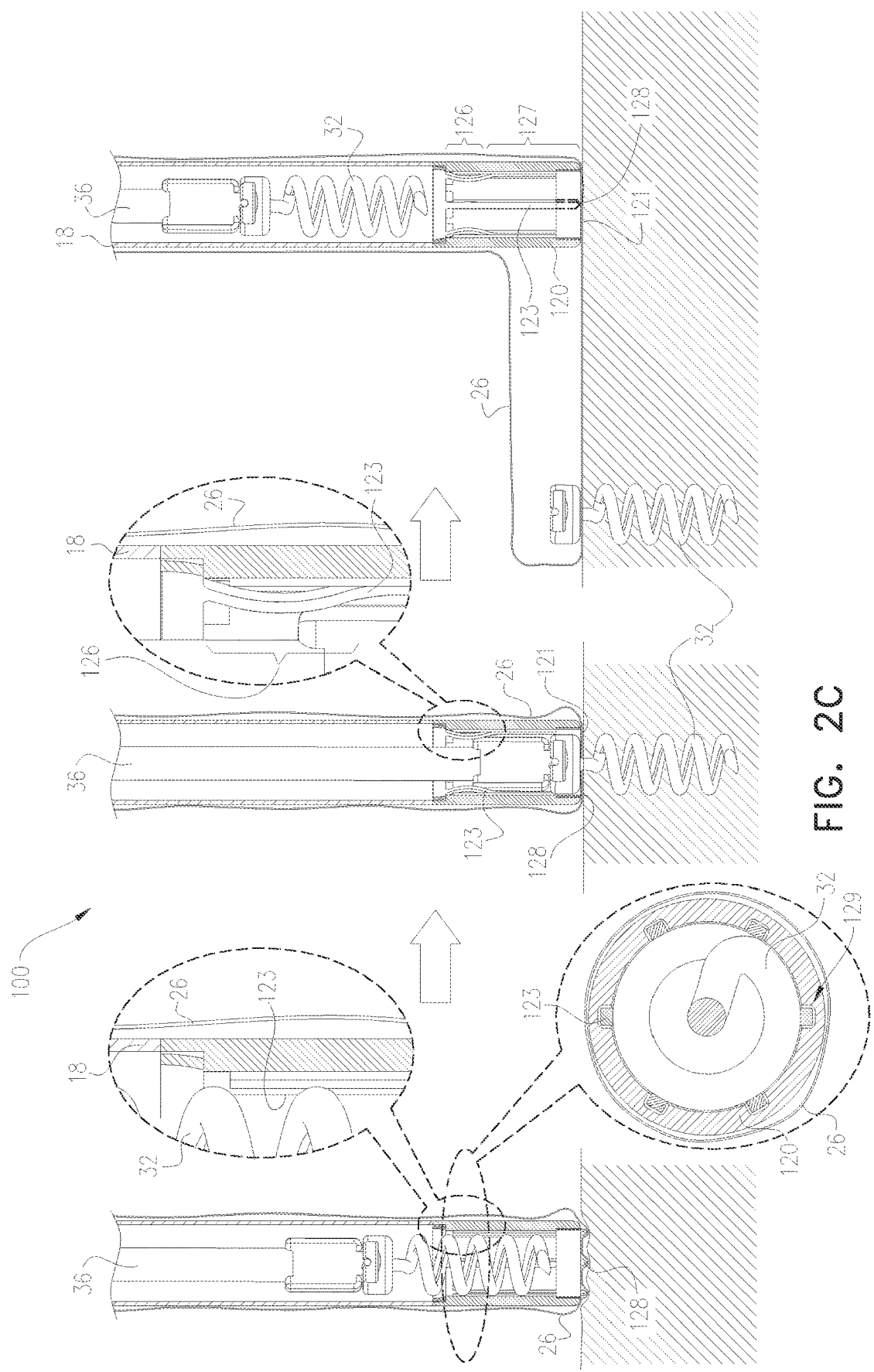

Reference is now made to FIGS. 2A-C, which are schematic illustrations of a system 100 comprising one or more rotationally-controlled steering catheters configured for delivering an implant to a heart of a subject, in accordance with some applications of the present invention. System 100 is similar to system 10 described hereinabove with reference to FIG. 1, with the exception that implant-gripping element 40 comprises a deformable element 41 disposed within a housing 120. For some applications of the present invention, housing 120 is tubular and is shaped so as to define a lumen therethrough. Housing 120 is coupled to a distal end portion of a tube of channel 18. For some applications of the present invention, housing 120 defines the distal end portion of channel 18. For some applications of the present invention, a distal end 121 of housing 120 defines the distal end of channel 18. Deformable element 41 comprises a plurality of tines 123 disposed circumferentially with respect to an inner surface of housing 120, i.e., with respect to a distal end portion of channel 18. A proximal end of each tine 123 is coupled to a ring in order to couple together tines 123 and orient tines 123 circumferentially with respect to the distal end portion of channel 18. For some applications of the present invention, tines 123 comprise radiopaque material.

Deformable element 41 has a resting state (as shown in FIG. 2A) and a gripping state (as shown in FIG. 2B). Each tine 123 comprises a curved portion 126 and a straight portion 127 and a gripper 128 (e.g., a tooth) at a distal end of the straight portion. In the resting state of deformable element 41, curved portion 126 curves convexly toward and into the lumen of housing 120 such that the overall length of tine 123 is shortened. In the resting state of deformable element 41, gripper 128 is disposed within housing 120 and does not extend beyond a distal end 121 of housing 120 (i.e., gripper 128 does not extend beyond a distal end of channel 18). In the resting state, anchor 32 is disposed proximally to curved portions 126 of deformable element 41.

FIG. 2B shows deformable element 41 in its gripping state. In the gripping state, anchor 32 is disposed within the lumen of housing 120 and radially, or laterally, pushes against curved portions 126 of tines 123 so as to change a structural configuration of deformable element 41 by straightening curved portions 126 and responsively, longitudinally lengthening the overall length of each tine 123 and thereby longitudinally lengthening deformable element 41. Anchor 32 is disposed within the lumen of housing 120 and radially, or laterally, pushes against curved portions 126 in order to transition deformable element 41 from its resting state to its gripping state. In the gripping state, gripper 128 of each tine 123 is disposed distally to distal end 121 of housing 120, and thereby distally to a distal end of channel 18. In this state, gripper 128 is exposed from within housing 120 so that it is able to grip, press against, ensnare, or otherwise reversibly couple gripping element 40 to sleeve 26. The plurality of elongate tines 123 are configured to increase surface area contact with inner wall 50 of the implant in the gripping state of deformable element 41.

In the resting state of deformable element 41, as shown in FIG. 2A, grippers are disposed within housing 120 such that they do not ensnare sleeve 26 during advancement of channel 18 with respect to sleeve 26. Only once a tissue anchor 32 is passed through the distal end portion of channel 18, and through housing 120, as shown in FIG. 2B, deformable element 41 is engaged and grippers 128 are exposed.

FIG. 2C shows the steps involved in implanting two anchors 32 through material of sleeve 26. In the first step, a first anchor 32 is passed through housing 120 in a manner in which anchor 32 pushes radially against curved portions 126 of tines 123 such that portion 126 are straightened and the overall length of tines 123 increases, as shown in FIG. 2B. In this step, the distal grippers 128 engage sleeve 26 by pushing sleeve 26 slightly distally enough to engage sleeve 26 but not penetrate sleeve 26. This distal pushing increases friction between channel 18 and the implant. The portion of sleeve 26 engaged and gripped by grippers 128 is the portion of sleeve 26 that is sandwiched between distal end 121 of housing 120 (i.e., the distal end of channel 18) and tissue. Surface area between grippers 128 and sleeve 26 increases. As shown in the first step, housing 120 defines a plurality of inner grooves 129 which house a respective tine 123. As anchor 32 is being driven through fabric of sleeve 26 from within the lumen of sleeve 26, and into tissue of the subject, grippers 128 of deformable element 41 of anchor-gripping element 40 reversibly grip and hold in place sleeve 26 in order to prevent or minimize distortion, movement, deformation, twisting, torsion, bunching, and any other relative movement of sleeve 26 with respect to tissue. For applications in which tissue-coupling element 60 of anchor 32 comprises a helical tissue coupling-element, implant-gripping element 40 prevents or minimizes twisting or torsion of sleeve 26 during the driving of anchor 32 through the material of sleeve 26.

In the second step of FIG. 2C, anchor 32 has been driven fully into tissue. Once anchor 32 is driven into tissue, the radial force against curved portions 126 is absent, and curved portions 126 each return to their resting state of a curved shape, as shown in FIG. 2A, and the overall length of tine 123 decreases. Decreasing the length of tine 123 retracts grippers 128 into housing 120 such that they no longer contact sleeve 26. Since sleeve 26 is firmly anchored to tissue of the annulus, this slight upward movement of tines 123 overcomes the reversible grip grippers 128 temporarily have on sleeve 26.

It is to be noted that the radial force on curved portions 126 may be provided by tissue-coupling element 60 of anchor 32 and/or by tool-engaging head 62 of anchor, and/or by any part of anchor driver 36. For such applications, radial force against curved portions 126 may be maintained only until anchor driver 36 and/or anchor 32 has been removed from within housing 120 (i.e., in a state in which housing 120 is empty, as shown in the third step of FIG. 2C).

In the third step of FIG. 2C, deformable element 41 is in its resting state awaiting the advancement through housing 120 of an additional anchor. In the resting state, grippers 128 are disposed within housing 120 and do not extend beyond distal end 121 of housing 120, and thereby of channel 18. Since grippers 128 do not extend beyond distal end 121, deformable element 41 is in its resting state as shown in FIG. 2A, and implant-gripping element 40 does not engage sleeve 26. This stage in which implant-gripping element 40 does not engage sleeve 26 enables channel 18 to move unobstructedly through the lumen of sleeve 26 without ensnaring or inadvertently gripping or engaging sleeve 26 from within the lumen of sleeve 26. Thus, housing 120 and the overall structural configuration of deformable element 41 in its resting state enables such free movement of channel 18 within the lumen of sleeve 26. This is advantageous because channel 18 is able to move freely within a lumen of sleeve 26 and only engage and grip sleeve 26 once the desired location of tissue has been reached and it has been determined that in this location, a tissue anchor 32 be driven into tissue.

It is to be noted that the gripping and ungripping of gripping element 40 occurs repeatedly throughout the process of anchoring sleeve 26 to tissue of the annulus. For each anchor delivery, gripping element 40 grips sleeve 26 as each anchor 32 is deployed to anchor a given portion of the implant to the annulus, and once anchor 32 has been deployed, gripping element 40 is pulled proximally in order to reverse the gripping of sleeve 26 by gripping element 40. Channel 18 is then moved to a different portion of the implant, and the gripping of sleeve 26 by gripping element 40 occurs once more as another anchor is deployed to anchor the different portion of the implant to the annulus.

Figure 3B:
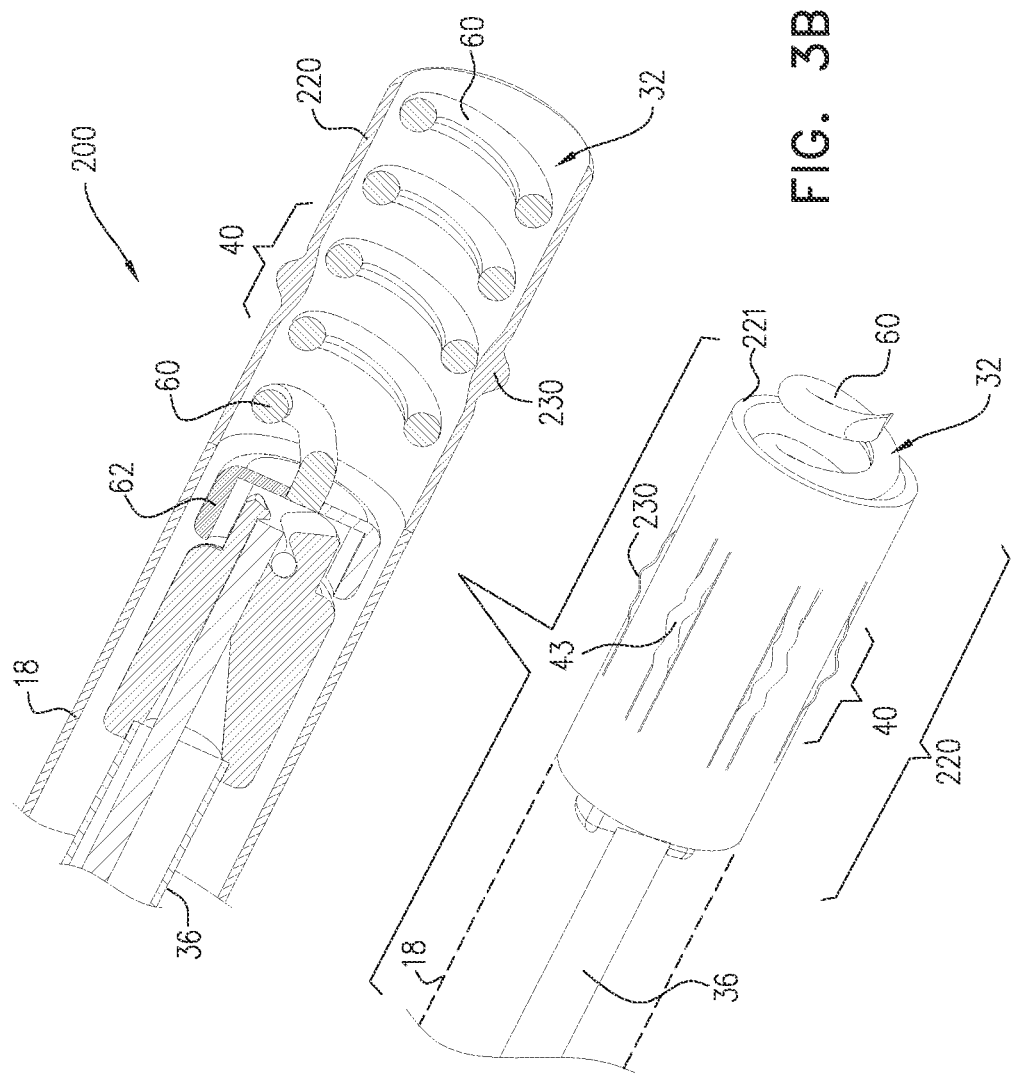
Figure 3C:
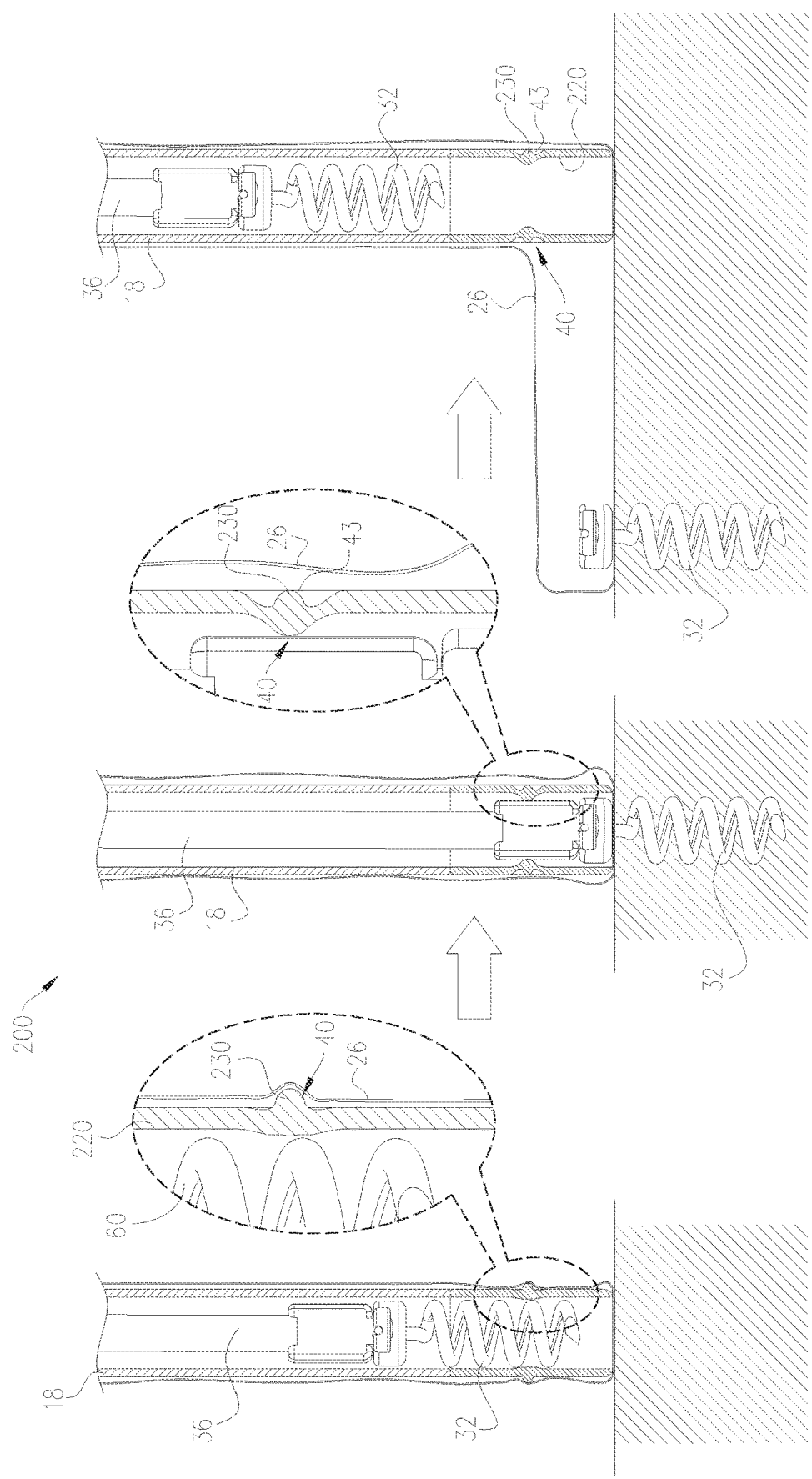

Reference is now made to FIGS. 3A-C, which are schematic illustrations of a system 200 comprising one or more rotationally-controlled steering catheters configured for delivering an implant to a heart of a subject, in accordance with some applications of the present invention. System 200 is similar to system 10 described hereinabove with reference to FIG. 1, with the exception that implant-gripping element 40 comprises a deformable element 41 of a housing 220. System 200 is similar to system 100 described hereinabove with reference to FIGS. 2A-C, with the exception that implant-gripping element 40 comprises a deformable element 41 comprising laterally-moveable lateral projections 230. For some applications of the present invention, housing 220 is tubular and is shaped so as to define a lumen therethrough. Housing 220 is coupled to a distal end portion of a tube of channel 18. For some applications of the present invention, housing 220 defines the distal end portion of channel 18. For some applications of the present invention, a distal end 221 of housing 220 defines the distal end of channel 18. Deformable element 41 comprises a plurality of laterally-moveable lateral projections 230 disposed circumferentially with respect to housing 220, i.e., slightly proximally with respect to a distal end portion of channel 18. For some applications of the present invention, projections are disposed at a middle section of housing 220, by way of illustration and not limitation. In such a manner, projections 230 grip the lateral portions of sleeve 26 as sleeve 26 hugs channel 18 and/or housing 220. The plurality of projections 230 are configured to increase surface area contact with inner wall 50 of the implant in the gripping state of deformable element 41.

For some applications of the present invention, projections 230 comprise radiopaque material.

Deformable element 41 has a resting state (as shown in FIG. 3A) and a gripping state (as shown in FIG. 3B). Each laterally-moveable lateral projections 230 comprises a lateral-most portion 43. In the resting state of deformable element 41, lateral-most portion 43 is aligned with a lateral surface of housing 220, i.e., with a lateral surface of channel 18. In the resting state of deformable element 41, portion 43 is disposed aligned with housing 220 and does not extend laterally beyond an external surface of housing 220. For some applications of the present invention, an inwardly-facing portion of projection 230 is disposed within the lumen of housing 220. In the resting state, anchor 32 is disposed proximally to projections 230 of deformable element 41.

FIG. 3B shows deformable element 41 in its gripping state. In the gripping state, anchor 32 is disposed within the lumen of housing 220 and radially, or laterally, pushes against laterally-moveable lateral projections 230 so as to change a structural configuration of deformable element 41 by extending lateral-most portions 43 of projections 230 beyond the lateral surface of anchor-delivery channel 18. As described hereinabove, an inwardly-facing portion of projection 230 is disposed within the lumen of housing 220 in a manner in which anchor 32 pushes against this inwardly-facing portion of projection 230 in order to outwardly push against projection 230 in order to transition deformable element 41 from its resting state to its gripping state. In the gripping state, lateral-most portions 43 of each projection 230 is disposed laterally with respect to housing 220. In this state, projection 230 projects away from housing 220 so that it is able to grip, press against, ensnare, or otherwise reversibly couple gripping element 40 to sleeve 26.

In the resting state of deformable element 41, as shown in FIG. 3A, portions 43 are aligned with the surface of housing 220 such that they do not ensnare sleeve 26 during advancement of channel 18 with respect to sleeve 26. Only once a tissue anchor 32 is passed through the distal end portion of channel 18, and through housing 220, as shown in FIG. 3B, deformable element 41 is engaged and projections 230 project beyond a lateral surface of housing 220.

FIG. 3C shows the steps involved in implanting two anchors 32 through material of sleeve 26. In the first step, a first anchor 32 is passed through housing 220 in a manner in which anchor 32 pushes radially against projections 230 of such that distal-most portions 43 project away from the external surface of housing 220, as shown in FIG. 3B. In this step, the projections 230 engage sleeve 26 by pushing sleeve 26 slightly laterally enough to engage sleeve 26 but not penetrate sleeve 26. This lateral pushing increases friction between channel 18 and the implant. Surface area between projections 230 and sleeve 26 increases. As anchor 32 is being driven through fabric of sleeve 26 from within the lumen of sleeve 26, and into tissue of the subject, projections 230 of deformable element 41 of anchor-gripping element 40 reversibly grip and hold in place sleeve 26 in order to prevent or minimize distortion, movement, deformation, twisting, torsion, bunching, and any other relative movement of sleeve 26 with respect to tissue. For applications in which tissue-coupling element 60 of anchor 32 comprises a helical tissue coupling-element, implant-gripping element 40 prevents or minimizes twisting or torsion of sleeve 26 during the driving of anchor 32 through the material of sleeve 26.

In the second step of FIG. 3C, anchor 32 has been driven fully into tissue. Once anchor 32 is driven into tissue, the radial force against projections 230 is absent, and projections 230 each return to their resting state by retracting laterally, as shown in FIG. 3A, and proximal-most portions 43 align with the external surface of housing 220. Retracting projections 230 laterally moves lateral-most portions 43 inwardly radially such that they no longer contact sleeve 26. Since sleeve 26 is firmly anchored to tissue of the annulus, this slight inward radial movement of projections 230 overcomes the reversible grip projections 230 temporarily have on sleeve 26.

It is to be noted that the radial force on projections 230 can be provided by tissue-coupling element 60 of anchor 32 and/or by tool-engaging head 62 of anchor, and/or by any part of anchor driver 36. For such applications, radial force against projections 230 may be maintained only until anchor driver 36 and/or anchor 32 has been removed from within housing 220 (i.e., in a state in which housing 220 is empty, as shown in the third step of FIG. 3C).

In the third step of FIG. 3C, deformable element 41 is in its resting state awaiting the advancement through housing 220 of an additional anchor. In the resting state, proximal-most portions 43 of projection 230 align with the external surface of housing 220 and do not extend beyond the lateral surface of housing 220, and thereby of channel 18. Portions 43 of projections 230 do not extend beyond the lateral surface of housing 220, deformable element 41 is in its resting state as shown in FIG. 3A, and implant-gripping element 40 does not engage sleeve 26. This stage in which implant-gripping element 40 does not engage sleeve 26 enables channel 18 to move unobstructedly through the lumen of sleeve 26 without ensnaring or inadvertently gripping or engaging sleeve 26 from within the lumen of sleeve 26. Thus, housing 220 and the overall structural configuration of deformable element 41 in its resting state enables such free movement of channel 18 within the lumen of sleeve 26. This is advantageous because channel 18 is able to move freely within a lumen of sleeve 26 and only engage and grip sleeve 26 once the desired location of tissue has been reached and it has been determined that in this location, a tissue anchor 32 be driven into tissue.

It is to be noted that the gripping and ungripping of gripping element 40 occurs repeatedly throughout the process of anchoring sleeve 26 to tissue of the annulus. For each anchor delivery, gripping element 40 grips sleeve 26 as each anchor 32 is deployed to anchor a given portion of the implant to the annulus, and once anchor 32 has been deployed, gripping element 40 is pulled proximally in order to reverse the gripping of sleeve 26 by gripping element 40. Channel 18 is then moved to a different portion of the implant, and the gripping of sleeve 26 by gripping element 40 occurs once more as another anchor is deployed to anchor the different portion of the implant to the annulus.

Reference is now made to FIGS. 1-3C. For some applications, systems 10, 100, and 200 are used in combination with one or more techniques and or devices, systems, etc. described in one or more of the following references, which are all incorporated herein by reference:

U.S. patent application Ser. No. 12/437,103 to Zipory et al., filed May 7, 2009, which published as US 2010/0286767. For example, (1) systems 10, 100, and 200 of the present application may be used to facilitate the techniques described with reference to FIGS. 2-3 and/or 6A-12 of US 2010/0286767 to Zipory et al., *mutatis mutandis*; (2) anchor driver 36 of the present application may comprise or correspond to anchor driver 68 and/or anchor deployment manipulator 24 of US 2010/0286767 to Zipory et al., *mutatis mutandis*; (3) tissue anchor 32 of the present application may comprise or correspond to anchor 38 of US 2010/0286767 to Zipory et al., *mutatis mutandis*; and/or (4) the implant of the present application may comprise or correspond to annuloplasty ring 22 of US 2010/0286767 to Zipory et al., *mutatis mutandis*.

U.S. patent application Ser. No. 12/689,635 to Zipory et al., filed Jan. 19, 2010, which published as US 2010/0280604. For example, (1) systems 10, 100, and 200 of the present application may be used to facilitate the techniques described with reference to FIGS. 2-3 and/or 11A-17 of US 2010/0280604 to Zipory et al., *mutatis mutandis*; (2) anchor driver 36 of the present application may comprise or correspond to anchor driver 68 and/or anchor deployment manipulator 24 of US 2010/0280604 to Zipory et al., *mutatis mutandis*; (3) tissue anchor 32 of the present application may comprise or correspond to anchor 38 of US 2010/0280604 to Zipory et al., *mutatis mutandis*; and/or (4) the implant of the present application may comprise or correspond to annuloplasty ring 22 of US 2010/0280604 to Zipory et al., *mutatis mutandis*.

PCT patent application IL2012/050451 to Sheps et al., filed Nov. 8, 2013, which published as WO 2013/069019. For example, (1) systems 10, 100, and 200 of the present application may be used to facilitate the techniques described with reference to FIGS. 14A-I of WO 2013/069019 to Sheps et al., *mutatis mutandis*; (2) systems 10, 100, and 200 of the present application may comprise or correspond to system 10 of WO 2013/069019 to Sheps et al., *mutatis mutandis*; (3) anchor driver 36 of the present application may comprise or correspond to anchor deployment manipulator 61 and/or anchor driver 36 of WO 2013/069019 to Sheps et al., *mutatis mutandis*; and/or (4) the implant of the present application may comprise or correspond to annuloplasty structure 222 and/or sleeve 26 of WO 2013/069019 to Sheps et al., *mutatis mutandis*.

PCT patent application IL2013/050860 to Sheps et al., titled "Controlled steering functionality for implant-delivery tool", filed on Oct. 23, 2013, which published as WO 2014/064694. For example, (1) systems 10, 100, and 200 of the present application may be used to facilitate techniques described with reference to FIGS. 10A-I, 12A-14B, 18A-C, 21-28, 34, and 36 of this PCT application titled "Controlled steering functionality for implant-delivery tool", *mutatis mutandis*; (2) systems 10, 100, and 200 of the present application may comprise or correspond to system 10 of this PCT application titled "Controlled steering functionality for implant-delivery tool", *mutatis mutandis*; anchor driver 36 of the present application may comprise or correspond to anchor deployment manipulator 61, anchor driver 36 and/or deployment element 2338 of this PCT application titled "Controlled steering functionality for implant-delivery tool", *mutatis mutandis*; and/or (4) the implant of the present application may comprise or correspond to annuloplasty structure 222 and/or sleeve 26 of this PCT application titled "Controlled steering functionality for implant-delivery tool", *mutatis mutandis*.

PCT patent application IL2013/050861 to Herman et al., titled "Percutaneous tissue anchor techniques", filed on Oct. 23, 2013, which published as WO 2014/064695. For example, (1) systems 10, 100, and 200 of the present application may be used to facilitate the techniques described with reference to FIGS. 9A-C and/or 13A-D of this PCT application titled "Percutaneous tissue anchor techniques", *mutatis mutandis*; (2) tissue anchor 32 of the present application may comprise or correspond to tissue anchor 40 of this PCT application titled "Percutaneous tissue anchor techniques", *mutatis mutandis*; and/or (3) anchor driver 36 of the present application may comprise or correspond to anchor driver 500, anchor driver 236, deployment manipulator 261, or tool 80 of this PCT application titled "Percutaneous tissue anchor techniques", *mutatis mutandis*.

PCT patent application IL2019/050777 to Brauon et al., titled "Annuloplasty Systems and Locking Tools Therefor", filed on Jul. 11, 2019, which published as WO 2020/012481.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. Further, techniques, methods, operations, steps, etc. described or suggested herein can be performed on a living animal or on a non-living simulation, such as on a cadaver, cadaver heart, simulator (e.g. with the body parts, tissue, etc. being simulated), etc.

The invention claimed is:

1. An apparatus, for use with a tissue anchor, the apparatus comprising:
    an implant, dimensioned to be advanced into a body of a subject; and
    an anchor-delivery tool comprising:
        an anchor-delivery channel shaped to define a lumen therethrough, the channel being dimensioned to be moveable within the implant; and
        an implant-gripping element, disposed at a distal end portion of the anchor-delivery channel, and comprising multiple teeth configured to reversibly grip an inner wall of the implant during implantation of the tissue anchor via the anchor-delivery channel.

2. The apparatus according to claim 1, wherein the implant-gripping element comprises a radiopaque material.

3. The apparatus according to claim 1, wherein the implant comprises a flexible material, and wherein the flexible material of the implant encases the distal end portion of the channel.

4. The apparatus according to claim 1, wherein the teeth are reversibly exposable from the distal end portion of the anchor-delivery channel.

5. The apparatus according to claim 1, wherein:
    each of the teeth is defined by a distal tip of a respective elongate element that is aligned with a longitudinal axis of the distal end portion of the anchor-delivery channel,
    a portion of the implant surrounds the elongate elements, and
    the elongate elements are spaced apart from one another such that the elongate elements are configured to grip the portion of the implant.

6. The apparatus according to claim 1, wherein the implant comprises a braided fabric, and wherein the teeth are configured to reversibly ensnare the braided fabric.

7. The apparatus according to claim 1, further comprising the tissue anchor, wherein the tissue anchor comprises:
    an anchor head; and
    a tissue-engaging member, coupled to the anchor head, extending distally away from the anchor head until a distal tip of the tissue-engaging member, and configured to anchor the anchor to tissue.

8. The apparatus according to claim 7, wherein the tissue-engaging member comprises a helical tissue-engaging member, and wherein the implant-gripping element is configured to reversibly grip the implant and prevent twisting of the implant during corkscrewing of the helical tissue-engaging member with respect to the implant.

9. The apparatus according to claim 1, further comprising the tissue anchor, and an anchor driver configured to slide the tissue anchor through the lumen of the anchor-delivery channel, the anchor driver comprising:
a shaft; and
a deployment element coupled to a distal end of the shaft, and reversibly couplable to the anchor.

10. The apparatus according to claim 1, further comprising the tissue anchor, wherein the implant-gripping element comprises a deformable element configured to change shape from a resting state to a gripping state in response to passage of the tissue anchor alongside the deformable element.

11. The apparatus according to claim 10, wherein the implant-gripping element comprises a plurality of deformable elements disposed circumferentially with respect to the distal end portion of the anchor-delivery channel.

12. The apparatus according to claim 10, wherein:
the deformable element is shaped so as to define multiple elongate tines, each of the multiple teeth defined by a distal end of a respective one of the tines,
in the resting state, each of the tines has a curved portion, and
the anchor is dimensioned to change the implant-gripping element into the gripping state by radially pushing against and straightening the curved portion of each of the tines.

13. The apparatus according to claim 12, wherein, in the gripping state, the teeth are exposed beyond the distal end portion of the anchor-delivery channel.

14. The apparatus according to claim 10, wherein:
the deformable element is shaped so as to define a lateral projection,
in the resting state, a lateral-most portion of the lateral projection is aligned with a lateral surface of the anchor-delivery channel, and
in the gripping state, the anchor is configured to radially push against the lateral projection so as to move the lateral-most portion of the lateral projection laterally beyond the lateral surface of the anchor-delivery channel.

15. The apparatus according to claim 14, wherein the at least one deformable element comprises a plurality of lateral projections, and wherein the anchor is configured to radially push against the plurality of lateral projections.

16. The apparatus according to claim 15, wherein the plurality of lateral projections are configured to increase surface area contact with the inner wall of the implant in the gripping state of the deformable element.

17. A system, comprising:
an implant, dimensioned to be advanced into a body of a subject;
a tissue anchor, and
an anchor-delivery tool comprising:
an anchor-delivery channel shaped to define a lumen therethrough, the channel being dimensioned to be moveable within the implant; and
an implant-gripping element:
disposed at a distal end portion of the channel, comprising a deformable element, and
configured to reversibly grip the implant by the deformable element changing from a resting state to a gripping state responsively to passage of the tissue anchor through the channel alongside the deformable element.

18. The system according to claim 17, wherein the implant-gripping element comprises a radiopaque material.

19. The system according to claim 17, wherein the implant comprises a flexible material, and wherein the flexible material of the implant encases the distal end portion of the channel.

20. The system according to claim 17, wherein the implant-gripping element comprises multiple teeth.

21. The system according to claim 20, wherein the implant comprises a braided fabric, and wherein the teeth are configured to reversibly ensnare the braided fabric.

22. The system according to claim 17, wherein the tissue anchor comprises:
an anchor head; and
a tissue-engaging member, coupled to the anchor head, extending distally away from the anchor head until a distal tip of the tissue-engaging member, and configured to anchor the anchor to tissue.

23. The system according to claim 22, wherein the tissue-engaging member comprises a helical tissue-engaging member, and wherein the implant-gripping element is configured to reversibly grip the implant and prevent twisting of the implant during corkscrewing of the helical tissue-engaging member with respect to the implant.

24. The system according to claim 17, wherein the anchor-delivery tool further comprises an anchor driver slidable through the lumen of the anchor-delivery channel, the anchor driver comprising:
a shaft; and
a deployment element coupled to a distal end of the shaft, and reversibly couplable to the tissue anchor.

25. The system according to claim 17, wherein the implant-gripping element comprises a plurality of deformable elements disposed circumferentially with respect to the distal end portion of the anchor-delivery channel.

26. The system according to claim 17, wherein the implant-gripping element comprises a tooth, configured such that changing of the implant-gripping element to the gripping state extends the tooth distally from the distal end portion of the channel.

27. The system according to claim 26, wherein:
the deformable element comprises an elongate tine, the tooth defined by a distal end of the tine,
in the resting state, the tine has a curved portion, and
the anchor is dimensioned to change the implant-gripping element into the gripping state by radially pushing against and straightening the curved portion of the tine.

28. The system according to claim 27, wherein:
the tooth is one of multiple teeth,
the implant-gripping element comprises multiple elongate tines, each of the multiple teeth defined by a respective distal end of a respective one of the tines, and
the anchor is dimensioned to change the implant-gripping element into the gripping state by radially pushing against and straightening the curved portion of each of the tines.

29. The system according to claim 17, wherein:
the deformable element is shaped so as to define a lateral projection,
in the resting state, a lateral-most portion of the lateral projection is aligned with a lateral surface of the anchor-delivery channel, and
in the gripping state, the anchor is configured to radially push against the lateral projection so as to move the lateral-most portion of the lateral projection laterally beyond the lateral surface of the anchor-delivery channel.

30. The system according to claim 29, wherein the implant-gripping element comprises multiple deformable elements, each of the deformable elements defining a respective lateral projection, and wherein the anchor is configured to radially push against the multiple deformable elements.

\* \* \* \* \*